(12) United States Patent
Shimada et al.

(10) Patent No.: US 11,209,392 B2
(45) Date of Patent: Dec. 28, 2021

(54) SIMPLIFIED MONOCLONAL ANTIBODY QUANTIFICATION METHOD

(71) Applicant: Shimadzu Corporation, Kyoto (JP)

(72) Inventors: Takashi Shimada, Kyoto (JP); Noriko Iwamoto, Kyoto (JP); Megumi Takanashi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/954,649

(22) PCT Filed: Dec. 28, 2017

(86) PCT No.: PCT/JP2017/047190
§ 371 (c)(1),
(2) Date: Jun. 17, 2020

(87) PCT Pub. No.: WO2019/130536
PCT Pub. Date: Jul. 4, 2019

(65) Prior Publication Data
US 2020/0309735 A1    Oct. 1, 2020

(51) Int. Cl.
*G01N 27/62* (2021.01)
*C12N 11/14* (2006.01)
(Continued)

(52) U.S. Cl.
CPC .............. *G01N 27/62* (2013.01); *C12N 11/14* (2013.01); *G01N 30/06* (2013.01); *G01N 30/72* (2013.01)

(58) Field of Classification Search
CPC ........ G01N 27/62; G01N 30/06; G01N 30/72; C12N 11/14
(Continued)

(56) References Cited

U.S. PATENT DOCUMENTS

2016/0252522 A1    9/2016 Shimada et al.
2018/0051053 A1    2/2018 Shimada et al.
(Continued)

FOREIGN PATENT DOCUMENTS

EP          3495480 A1      6/2019
WO     2015/033479 A1      3/2015
(Continued)

OTHER PUBLICATIONS

International Search Report issued in corresponding International Patent Application No. PCT/JP2017/047190 dated Apr. 3, 2018.
(Continued)

*Primary Examiner* — Nicole M Ippolito
(74) *Attorney, Agent, or Firm* — Morgan, Lewis & Bockius LLP

(57) ABSTRACT

The present invention provides a method for detecting a monoclonal antibody in a sample, the method comprising: (a) a step of capturing and immobilizing, in pores of a porous body, the monoclonal antibody in the sample; (b) a step of performing selective protease digestion of the monoclonal antibody for 30 min or longer by contacting the porous body having the monoclonal antibody immobilized thereon with nanoparticles having a protease immobilized thereon; and (c) a step of detecting a peptide fragment obtained by the selective protease digestion, using liquid chromatography mass spectrometry (LC-MS), wherein step (b) is carried out under stirring condition for 10 sec to 5 min in the initial reaction stage, and then under static condition. According to the present invention, the detection method of a monoclonal antibody using mass spectrometry is simplified and can be applicable to multisample analysis.

5 Claims, 6 Drawing Sheets

Specification includes a Sequence Listing.

(51) Int. Cl.
*G01N 30/06* (2006.01)
*G01N 30/72* (2006.01)

(58) Field of Classification Search
USPC .................................. 250/281, 282, 283, 288
See application file for complete search history.

(56) References Cited

U.S. PATENT DOCUMENTS

| | | | |
|---|---|---|---|
| 2018/0051272 | A1 | 2/2018 | Shimada et al. |
| 2018/0052172 | A1 | 2/2018 | Shimada et al. |
| 2018/0059074 | A1* | 3/2018 | Shimada ............ G01N 33/6857 |
| 2018/0148763 | A1 | 5/2018 | Shimada et al. |
| 2020/0011876 | A1* | 1/2020 | Iwamoto .............. G01N 33/577 |
| 2020/0173960 | A1* | 6/2020 | Iwamoto ............ G01N 33/6854 |

FOREIGN PATENT DOCUMENTS

| | | |
|---|---|---|
| WO | 2016/143223 A1 | 9/2016 |
| WO | 2016/143224 A1 | 9/2016 |
| WO | 2016/143226 A1 | 9/2016 |
| WO | 2016/143227 A1 | 9/2016 |
| WO | 2016/194114 A1 | 12/2016 |
| WO | 2018/025346 A1 | 2/2018 |

OTHER PUBLICATIONS

Iwamoto et al., "Selective detection of complementarity-determining regions of monoclonal antibody by limiting protease access to the substrate: nano-surface and molecular-orientation limited proteolysis," Analyst, 139: 576-580 (2014).

Iwamoto et al., "The development of the validated LCMS bioanalysis of trastuzumab in human plasma using a selective detection method for complementarity-determining regions of monoclonal antibodies: nano-surface and molecular-orientation limited (nSMOL) proteolysis," Analytical Methods, 21: 9177-9183 (2015).

Iwamoto et al., "Fully validated LCMS bioanalysis of Bevacizumab in human plasma using nano-surface and molecular-orientation limited (nSMOL) proteolysis," Drug Metabolism and Pharmacokinetics, 31: 46-50 (2016).

Iwamoto et al., "Application of nano-surface and molecular-orientation limited proteolysis to LC-MS bioanalysis of cetuximab," Bioanalysis, 8 (10): 1009-1020 (2016).

Iwamoto et al., "Validated LC/MS Bioanalysis of Rituximab CDR Peptides Using Nano-surface and Molecular-Orientation Limited (nSMOL) Proteolysis," Biological and Pharmaceutical Bulletin, 39 (7): 1187-1194 (2016).

Iwamoto et al., "Validated LC-MS analysis of immune checkpoint inhibitor Nivolumab in human plasma using a Fab peptide selective quantitation method: nano-surface and molecular-orientation limited (nSMOL) proteolysis," Journal of Chromatography B, 1023-1024: 9-16 (2016).

Iwamoto et al., "Multiplex LCMS Bioanalysis of Brentuximab Vedotin, Rituximab and Cetuximab towards Therapeutic Drug Monitoring Application by Combined Calibration Curve Using Fab-Selective Limited Proteolysis nSMOL," Clinical Pharmacology & Biopharmaceutics, 5 (4): 1000164 (2016).

Iwamoto et al., "LC-MS bioanalysis of Trastuzumab and released emtansine using nano-surface and molecular-orientation limited (nSMOL) proteolysis and liquid-liquid partition in plasma of Trastuzumab emtansine-treated breast cancer patients," Journal of Pharmaceutical and Biomedical Analysis, 145: 33-39 (2017).

Written Opinion issued in corresponding International Patent Application No. PCT/JP2017/047190 dated Apr. 3, 2018 (see partial English translation).

Extended European Search Report issued in related European Patent Application No. 17935959.1 dated Sep. 8, 2021.

Iwamoto et al., "Antibody drug quantitation in coexistence with anti-drug antibodies on nSMOL bioanalysis," Analytical Biochemistry, 540-541: 30-37 (2018).

* cited by examiner

SIMPLIFIED MONOCLONAL ANTIBODY QUANTIFICATION METHOD

SEQUENCE LISTING SUBMISSION VIA EFS-WEB

A computer readable text file, entitled "SequenceListing.txt," created on or about Jun. 17, 2020 with a file size of about 2 kb contains the sequence listing for this application and is hereby incorporated by reference in its entirety.

TECHNICAL FIELD

The present invention relates to a simplified quantification method for a monoclonal antibody, and more specifically, to a quantification method adapted for an automatic quantification system using mass spectrometry. Still more specifically, the present invention relates to improvement of a protocol that has been established for quantification of a monoclonal antibody.

BACKGROUND ART

Recently, intensive efforts have been made to develop bio-analysis of antibody medicines by using LC-MS/MS technique as a quantification method in replacement of ELISA technique.

The group of the present inventors have found that protease digestion of a monoclonal antibody by a site-selective solid phase-solid phase reaction is possible by immobilizing both of the monoclonal antibody to be measured and a protease capable of digesting the monoclonal antibody as a substrate onto a solid phase, thereby successfully obtaining peptides specific to individual monoclonal antibodies (see Patent Literatures 1 to 6, and Non-Patent Literatures 1 to 8). This method is a pretreatment method for mass spectrometry in which Fab-region selective protease digestion of a monoclonal antibody is carried out in such a manner that a porous body having the monoclonal antibody immobilized in pores thereof is brought into contact with nanoparticles having a protease immobilized thereon in a liquid, and is a groundbreaking technology that allows effective detection and quantification of obtained peptide fragments by liquid chromatography mass spectrometry (LC-MS). The present inventors named this method as "nano-surface and molecular-orientation limited proteolysis method (nSMOL method)".

Quantification of a blood level of an antibody medicine by the nSMOL method is a method that carries out protease digestion selectively digesting only the Fab region having a sequence specific to the antibody medicine and that inhibits the ion suppression effect most problematic in the LC-MS/MS analysis, thereby making it possible to provide more stable and highly reliable quantification values. The present inventors have already confirmed that a quantification method of a monoclonal antibody using a combination of the nSMOL method and the LC-MS/MS method meets the standards of the guidelines for validation of biological analysis methods in Japan, the United States, and Europe, in terms of measuring blood levels of 15 or more kinds of antibody medicines.

CITATION LIST

Patent Literatures

Patent Literature 1: International Publication No. 2015/033479
Patent Literature 2: International Publication No. 2016/143223
Patent Literature 3: International Publication No. 2016/143224
Patent Literature 4: International Publication No. 2016/143226
Patent Literature 5: International Publication No. 2016/143227
Patent Literature 6: International Publication No. 2016/194114

Non Patent Literature

Non Patent Literature 1: Analyst. 2014 Feb. 7; 139(3): 576-80. doi: 10.1039/c3an02104a
Non Patent Literature 2: Anal. Methods, 2015; 21: 9177-9183. doi:10.1039/c5ay01588j
Non Patent Literature 3: Drug Metabolism and Pharmacokinetics, 2016; 31: 46-50. doi:10.1016/j.dmpk.2015.11.004
Non Patent Literature 4: Bioanalysis. 2016; 8(10):1009-20. doi: 10.4155. bio-2016-0018
Non Patent Literature 5: Biol Pharm Bull, 2016; 39(7):1187-94. doi: 10.1248/bpb.b16-00230
Non Patent Literature 6: J Chromatogr B Analyt Technol Biomed Life Sci; 2016; 1023-1024:9-16. doi: 10.1016/j.jchromb.2016.04.038
Non Patent Literature 7: Clin Pharmacol Biopharm 2016; 5:164. doi:10.4172/2167-065X.1000164
Non Patent Literature 8: J. Pharm Biomed Anal; 2017; 145:33-39. doi:10.1016/j.jpba.2017.06.032

SUMMARY OF INVENTION

Technical Problem

The nSMOL method has such a reaction mechanism that the protease solid-phased on the surface of nanoparticles of approximately 200 nm in diameter is contacted with antibody molecules immobilized in a porous body of approximately 100 nm in pore diameter, thereby selectively cutting Fab of the antibody molecules in a restricted reaction field. Therefore, it has been considered that, in order to proceed the selective protease digestion of the antibody molecules in the nSMOL method, the surface of the nanoparticles and the porous body should be contacted homogeneously with each other, and they must be homogeneously dispersed in a reaction solution by mixing or stirring during the reaction.

For example, a pretreatment kit for LC/MS/MS called "nSMOL Antibody BA Kit" (Shimadzu Corporation) is commercially available for carrying out the nSMOL method. The protocol provided together with the kit describes that stirring with a Vortex mixer or the like is carried out in contacting the nanoparticles with the porous body. With a microscale sample of micro litter order held right on the Vortex mixer, the reaction is proceeded under stirring, thereby attaining highly reproducible reaction.

On the other hand, the use of a Vortex mixer results in that a yield after the reaction is greatly dependent on influence from the vessel shape, especially, from the shape of the incubator, thus resulting in a kind of machine dependence.

Therefore, the nSMOL method can be carried out in general laboratories, but may be difficult for initial installation or in clinical laboratories in hospitals.

The vessel used in the nSMOL method should be in a form of microtube, and therefore it is considered that the nSMOL method is difficult to conduct with a tube of a special shape or a tube of a small capacity. Furthermore, the nSMOL method can be carried out with a microplate for multisample analysis, but there is a possibility that the stirring with a Vortex mixer cannot create a uniform reaction environment in this case. Therefore, stirring speed should be strictly controlled. As such, the nSMOL method is not so excellent in general versatility.

For stirring at a low speed, Patent Literature 4 (WO 2016/143226) mentioned above discloses a method in which tapping rotation stirring is carried out. This improved method still needs some improvements for general versatility.

Solution to Problem

In view of the aforementioned problems, the present inventors have made further studies on reaction conditions in order to improve the nSMOL method in general versatility.

More specifically, in order to eliminate the vessel particularity, the present inventors studied on conditions under which the nSMOL reaction can occur irrespectively of what kind of experiment apparatus is used. For example, the present inventors studied to improve the nSMOL method such that the method can be carried out with various apparatuses such as a block heater, a thermal cycler, a space-saving incubator, a water bath, or the like, apart from a box-shaped incubator capable of accommodating a water-filled tray therein.

As a result, the present inventors found out that, in carrying out the selective protease digestion of the monoclonal antibody by contacting the nanoparticles with the porous body, quantitative detection without a significant deterioration in detection results can be attained even if particles of both the nanoparticles and the porous body precipitated in the sample without continuous stirring during the digestion reaction.

That is, the present invention provides the followings.

1. A method for detecting a monoclonal antibody in a sample, the method comprising:

(a) a step of capturing and immobilizing, in pores of a porous body, the monoclonal antibody in the sample;

(b) a step of performing selective protease digestion of the monoclonal antibody for 30 min or longer by contacting the porous body having the monoclonal antibody immobilized thereon with nanoparticles having a protease immobilized thereon; and (c) a step of detecting a peptide fragment obtained by the selective protease digestion, using liquid chromatography mass spectrometry analysis (LC-MS), wherein step (b) is carried out under stirring condition for 10 sec to 5 min in an initial reaction stage, and then under static condition.

2. The method according to 1 above, wherein step (b) further comprises additional stirring for 10 sec to 1 min one or more times in addition to the stirring for 10 sec to 1 min in the initial reaction stage.

3. The method according to 1 or 2 above, wherein the stirring is carried out by pipetting operation performed by an automatic dispenser.

4. The method according to any one of 1 to 3 above, wherein step (b) is carried out in a heating vessel that is set to a predetermined reaction temperature.

5. The method according to any one of 1 to 4 above, capable of quantifying the monoclonal antibody in the sample having an antibody concentration in the range of 0.05 to 300 μg/ml.

Advantageous Effects of Invention

According to the present invention, the reaction technique can be simplified and it becomes possible to use a wider range of vessels in a wider range of experiment facilities for detecting monoclonal antibodies by the nSMOL method. Furthermore, it becomes possible to use a microplate for dealing with multi samples, thereby expecting applications of the nSMOL method to automated multisample analysis.

DESCRIPTION OF EMBODIMENTS

Figure 1:
FIG. 1 shows results of trastuzumab analysis under 3 reaction conditions. (A): step (b) is carried out for 1 hour; (B): step (b) is carried out for 3 hour; and (C): step (b) is carried out for 5 hour. A_1, A_3, and A_5 indicate results of cases where stirring was carried out throughout the analysis. B_1, B_3, and B_5 indicate results of cases where 10-sec stirring was carried out every 1 hour. C_3 and C_5 indicate results of cases where the samples were let stand after initial stirring. The vertical axes indicate the relative peak intensity.

The present invention provides a method for detecting a monoclonal antibody in a sample, comprising:

(a) a step of capturing and immobilizing, in pores of a porous body, the monoclonal antibody in the sample;

(b) a step of performing selective protease digestion of the monoclonal antibody for 30 min or longer by contacting the porous body having the monoclonal antibody immobilized thereon with nanoparticles having a protease immobilized thereon; and (c) a step of detecting a peptide fragment obtained by the selective protease digestion, by using liquid chromatography mass spectrometry (LC-MS), wherein step (b) is carried out under stirring condition for 10 sec to 5 min in a initial reaction stage, and then under static condition.

<Step (a)>

Step (a) of the method according to the present invention is a step of capturing and immobilizing, in pores of a porous body, the monoclonal antibody in the sample.

In this Description, a "sample" means a liquid sample in which the presence of a monoclonal antibody is to be detected, and is not particularly limited. In general, the sample is a biological sample derived from a mammal such as a mouse, a rat, a rabbit, a goat, a bovine, a human being, or the like, especially a human subject, or mainly a human patient, or preferably plasma, serum, or a tissue homogenate extract. Alternatively, the sample may be a liquid sample containing a monoclonal antibody and serum artificially added, to prove the effect of the present invention. For detecting a monoclonal antibody in a method according to the present invention, a concentration of the monoclonal antibody in the sample should be in the range of 0.05 to 300 µg/ml.

Examples of the monoclonal antibody that can be a measurement target include, but not limited to, human antibodies such as panitumumab, ofatumumab, golimumab, ipilimumab, nivolumab, Ramucirumab, adalimumab, and the like; humanized antibodies such as Tocilizumab, trastuzumab, trastuzumab-DM1, bevacizumab, omalizumab, Mepolizumab, gemtuzumab, palivizumab, Ranibizumab, certolizumab, ocrelizumab, Mogamulizumab, Eculizumab, tocilizumab, mepolizumab, and the like; chimeric antibodies such as rituximab, cetuximab, infliximab, Basiliximab, and the like.

Furthermore, a conjugate having an additional function added while maintaining the specificity of a monoclonal antibody, for example, Fc-fused proteins (such as etanercept, abatacept, and the like) and antibody-drug conjugates (such as brentuximab vedotin, Gemtuzumab ozogamicin, Trastuzumab emtansine, and the like) may also be a monoclonal antibody as a measurement target. The conjugate may be pretreated to dissociate its bonding prior to the measurement, so that only its antibody portion can be provided to the analysis. As an alternative, the conjugate as such may be provided to the analysis.

Information on amino acid sequences of monoclonal antibodies, etc. can be obtained from, for example, Kyoto Encyclopedia of Genes and Genomes, KEGG.

The porous body for use in the method according to the present invention may be a material having a large number of pores and being capable of binding with an antibody site-specifically. An average pore diameter of the porous body is approximately in range of 10 nm to 200 nm, and set as appropriate to be smaller than the average particle diameter of the nanoparticles.

In step (a) in the present invention, a monoclonal antibody as a measurement target is immobilized in pores of a porous body. For this purpose, a porous body, in pores of which linker molecules interactive with the antibody site-specifically are immobilized may be preferably used.

The linker molecules may be preferably Protein A, Protein G, or the like, capable of site-specifically binding with the Fc domain of the antibody. The use of a porous body with such linker molecules immobilized in the pores thereof allows the Fc domain of the antibody to be anchored in the pores in such a way that the Fab domain is located near the surface layer in the pores, thereby allowing site-selective digestion of the Fab domain by the protease.

A porous body that can be suitably used in the present invention is not particularly limited. For example, Protein G Ultralink resin (manufactured by Pierce Corporation), Toyopearl TSKgel (manufactured by TOSOH Corporation), Toyopearl AF-rProtein A HC-650F resin (manufactured by TOSOH Corporation), Protein A Sepharose (GE Healthcare), KanCapA (KANEKA), and the like can be used.

A method for immobilizing an antibody in pores of a porous body is not particularly limited. For example, when an antibody is immobilized in a porous body in which Protein A or Protein G is immobilized in pores in advance, the antibody can be easily immobilized in pores by mixing a suspension of the porous body with a solution containing the antibody. A quantitative ratio of the porous body to the antibody can be appropriately set according to a purpose.

<Step (b)>

Step (b) of the method according to the present invention is a step of carrying out selective protease digestion of the monoclonal antibody for 30 min or longer by contacting the porous body with nanoparticles, the porous body being obtained in step (a) to have the monoclonal antibody immobilized thereon, and the nanoparticles having a protease immobilized thereon.

The protease to be immobilized on nanoparticles may be appropriately selected depending on the monoclonal antibody to be quantified or identified by mass spectrometry, and is not limited. Examples of the protease include trypsin, chymotrypsin, lysyl endopeptidase, V8 protease, Asp N protease (Asp-N), Arg C protease (Arg-C), papain, pepsin, dipeptidyl peptidase used alone or in combination. As the proteases, trypsin is particularly preferably used. Examples of the protease that can be suitably used in the method of the present invention include Trypsin Gold (manufactured by Promega Corporation), Trypsin TPCK-Treated (manufactured by Sigma Corporation), and the like.

The nanoparticles have a larger average particle size than the average pore diameter of the porous body. The shape of the nanoparticles are not particularly limited. However, from a point of view of homogenization of access of the protease to the pores of the porous body, spherical nanoparticles are preferred. Further, it is preferable that the nanoparticles have high dispersibility and a uniform particle size.

As a type of the nanoparticles, magnetic nanoparticles that can be dispersed or suspended in an aqueous medium and can be easily recovered from the dispersion or suspension by magnetic separation or magnetic precipitation separation are preferable. Further, from a point of view that aggregation is less likely to occur, magnetic nanoparticles coated with an organic polymer are more preferable. Specific examples of magnetic nanobeads coated with an organic polymer include FG beads, SG beads, Adembeads, nanomag, and the like. As a commercially available product, for example, FG beads (polymer magnetic nanoparticles having a particle size of about 200 nm obtained by coating ferrite particles with polyglycidyl methacrylate (poly GMA)) manufactured by Tamagawa Seiki Co., Ltd. is suitably used.

In order to suppress nonspecific protein adsorption and to selectively immobilize the protease, the nanoparticles are preferably modified with spacer molecules capable of binding to the protease. By immobilizing a protease via a spacer molecule, desorption of the protease from surfaces of the nanoparticles is suppressed, and site-selectivity of protease digestion can be improved. Further, by adjusting a molecular size of a spacer, a protease can be selectively access a desired position of an antibody, and thus site-selectivity can be improved.

Nanoparticles surface-modified with such spacer molecules are also commercially available, for example, nanoparticles modified with a spacer molecule having an ester group activated with N-hydroxysuccinimide (active ester group) are commercially available under a trade name of "FG beads NHS" (Tamagawa Seiki Co., Ltd.).

A method for immobilizing a protease on surfaces of nanoparticles is not particularly limited. An appropriate method can be adopted according to characteristics of the protease and the nanoparticles (or spacer molecules modifying the surfaces of the nanoparticles). The aforementioned pretreatment kit for LC/MS/MS "nSMOL Antibody BA Kit" (Shimadzu Corporation) includes "FG beads Trypsin DART®", which are nanoparticles on which trypsin is immobilized as a protease, which can suitably be used for the method of the present invention.

By contacting the porous body having the monoclonal antibody immobilized thereon with the nanoparticles having the protease immobilized thereon, the selective protease digestion of the monoclonal antibody is carried out, thereby producing peptide fragments.

For example, the protease digestion may be carried out in a buffer solution adjusted to be near optimum pH for the protease. The reaction temperature for the protease digestion may be at about 37° C., but it is preferable to carry out the protease digestion at about 50° C. under saturated vapor pressure. The reaction time may be in the range of 30 min to 20 hours, for example, 1 hour to 8 hours, or 3 hours to 5 hours.

In the method according to the present invention, step (b) is carried out under a stirring condition for a time period in a range of 10 seconds to 5 min, for example, in a range of 10 seconds to 1 min in the initial reaction stage and then under a static condition. The "initial reaction stage" herein means an initial portion of the time period of 30 min or longer in which step (b) is carried out. It would be understood that stirring precisely immediately after contacting the porous body with the nanoparticles may not be possible under various experiment environments. However, in general, the stirring is carried out at the stage of adding the nanoparticles having the protease immobilized thereon to the porous body having the monoclonal antibody immobilized thereon, or at the stage of adding the porous body having the monoclonal antibody immobilized thereon to the nanoparticles having the protease immobilized thereon.

The manner of the stirring is not particularly limited, and stirring with a Vortex mixer, a stirrer, a rotary mixer, or a tapping rotary mixer can be used. The stirring may be achieved by, for example, a pipetting operation with an automated dispenser, that is, sucking up and discharging of a reaction solution by a micro pipet.

Surprisingly, as proven in Examples, it was confirmed that, even without continuous stirring during the reaction as conventionally considered necessary, the reaction in step (b) could proceed successfully by sufficiently stirring before the reaction, thereby attaining quantitative detection of the monoclonal antibody in the sample.

Therefore, the stirring in the initial reaction stage is sufficient, and stirring thereafter is not necessarily required. However, the method according to the present invention does not exclude comprising, for example, additional stirring for 10 seconds to 1 min at least once after the stirring for 10 seconds to 1 min in the initial reaction stage in step (b).

As described above, the present invention can provide a more simplified method for detecting a monoclonal antibody, by carrying out the reaction of step (b) under the stirring condition in the initial reaction stage followed by the static condition.

In order to prevent evaporation of the reaction solution, it is preferable to maintain the reaction under the saturated vapor pressure. For this purpose, it is considered to place a small box filled with water inside a space-saving incubator, for example. For the heat block, a sample together with a wiper wetted with water may be sealed with a Saran Wrap (plastic wrap) or the like and heated. Even with such an ordinary technique, the nSMOL reaction can sufficiently proceed, thereby allowing bio-analysis of an antibody medicine. Furthermore, step (b) may be carried out in a heating vessel set to a predetermined reaction temperature. This arrangement may be effective for automation of the detection method.

Peptides obtained by the protease digestion are dissolved and released in the reaction solution. Therefore, in order to subject a target peptide fragment to mass spectrometry, it is necessary to remove the porous body and the nanoparticles. This can be achieved by subjecting a sample after the protease digestion to filtration, centrifugation, magnetic separation, dialysis, and the like.

For example, by filtration using a filtration membrane made of polyvinylidene fluoride (PVDF) (low-binding hydrophilic PVDF having a pore diameter of 0.2 μm manufactured by Millipore Corporation), a filtration membrane made of polytetrafluoroethylene (PTFE) (low-binding hydrophilic PTFE having a pore diameter of 0.2 μm manufactured by Millipore Corporation), and the like, the porous body and the nanoparticles can be easily removed. The filtration may be centrifugal filtration, thereby making it possible to carry out the filtration promptly and easily.

<Step (c)>

Step (c) of the method according to the present invention is a step of detecting, by using liquid chromatography mass spectrometry (LC-MS), the peptide fragments obtained by the selective protease digestion.

An ionization method in mass spectrometry and an analysis method of ionized sample are not particularly limited. Further, MS/MS analysis, multistage mass spectrometry of MS3 or higher, or multiple reaction monitoring (MRM) can also be performed using a triple quadrupole mass spectrometer or the like.

Examples of an apparatus especially suitable for the method of the present invention include, but not limited to, LCMS-8030, LCMS-8040, LCMS-8050, LCMS-8060 (all from Shimadzu Corporation), and LCMS-IT-TOF (Shimadzu Corporation).

With the mass spectrometry or the like to detect a peptide fragment including an amino acid sequence of a Fab region specific to a target monoclonal antibody, for example, CDR1 region, CDR2 region, or CDR3 region of a heavy chain and/or a light chain, it is possible to identify or quantify the target monoclonal antibody.

Amino acid sequence information etc. of monoclonal antibodies intended to be used as an antibody medicine have been published, so that information of amino acid sequences of heavy chains and light chains, Fab and Fc domains, complementarity determining regions (CDRs), disulphide bonding, etc. are available. The protease digestion according to the nSMOL method produces a plurality of peptides, and if amino acid sequence information of each of the peptides is available, it can be easily understood at which position in the monoclonal antibody the peptide exists. Therefore, it is possible to select an especially suitable peptide as an analysis target from among a plurality of peptides derived from Fab regions. Such a peptide thus selected is called "signature peptide".

Details of nSMOL method are disclosed, for example, in WO2015/033479; WO2016/143223; WO2016/143224; WO2016/143226; WO2016/143227; WO2016/194114; Analyst. 2014 Feb. 7; 139(3): 576-80. doi: 10.1039/c3an02104a; Anal. Methods, 2015; 21: 9177-9183. doi: 10.1039/c5ay01588j; Drug Metabolism and Pharmacokinetics, 2016; 31: 46-50. doi:10.1016/j.dmpk.2015.11.004; Bioanalysis. 2016; 8(10):1009-20. doi: 10.4155. bio-2016-0018; Biol Pharm Bull, 2016; 39(7):1187-94. doi: 10.1248/bpb.b16-00230; J Chromatogr B Analyt Technol Biomed Life Sci; 2016; 1023-1024:9-16. doi: 10.1016/j.jchromb.2016.04.038; Clin Pharmacol Biopharm 2016; 5:164. doi:10.4172/2167-065X.1000164; and J. Pharm Biomed Anal; 2017; 145:33-39. doi:10.1016/j.jpba.2017.06.032; and the like. The contents disclosed in these literatures are incorporated herein by reference.

EXAMPLES

The present invention will be described more concretely, referring to the following Examples, but the present invention is not limited to the Examples.

To begin with, the procedure of nSMOL method conducted in the Examples will be described below. Reagents and vessel etc. used may be those available from Shimadzu Corporation in the form of the "nSMOL Antibody BA Kit" together with the instructions.

The nSMOL Antibody BA kit includes the following reagents.

Immunoglobulin Collection Resin (suspension of a porous body according to the present invention)
Wash Solution 1 (washing solution)
Wash Solution 2 (washing solution)
Reaction Solution (reaction solution)
Enhanced Reaction Solution (reaction accelerating solution)
Reaction Stop Solution (reaction terminating solution)
FEG Beads Trypsin DART® (suspension of nanoparticles (particle diameter: 200 nm) with protease immobilized thereon)

A general protocol of the nSMOL method is as below.
<Step (a)>
Prepare 25 μL of Immunoglobulin Collection Resin (suspension).
Prepare and add 90 μL of Wash solution 1 to the above.
Prepare and add 10 μL of a sample (for example, human plasma) containing a monoclonal antibody to the above.
Gently stir the above for about 5 min.
Transfer the suspension into a filter cup or a filter plate.
Centrifuge the suspension (10,000 g×1 min, or 3,000 g×2 min) to remove the supernatant.
Add 200 μL of Wash solution 1 thereto and centrifuge in a similar manner to remove the supernatant (2 times).
Add 200 μL of Wash solution 2 thereto and centrifuge in a similar manner to remove the supernatant (2 times).
<Step (b)>
Add 75 μL of Reaction buffer or an Enhanced reaction buffer thereto.
Add 10 μL of FG beads Trypsin DART® thereto.
Stir the above at 50° C. under saturated vapor pressure for 5 hours.
Add 10 μL of Reaction Stop Solution.
Collect a solution by centrifugal filtration. The collecting is performed by the centrifugal filtration with magnetic separation or with a two-layered filter plates.
<Step (c)>
Perform LC-MS analysis.

Example 1

Using trastuzumab as a measurement target, the reaction at 50° C. in step (b) of the conventional general nSMOL method was carried out under the following three conditions for 5 hours, respectively. The stirring was carried out with a Vortex mixer (200-1000 rpm).
Condition A: Continuous stirring
Condition B: repeating a cycle of stirring for 1 min and then let stand for 1 hour (stirring every 1 hour)
Condition C: stirring for 1 min and then let stand
Samples prepared by adding trastuzumab of 50 μg/ml concentration (manufactured by Chugai Pharmaceutical Co., Ltd.) in Human plasma (manufactured by Kohjin Bio Co., Ltd.) were used, and the Enhanced Reaction Solution contained in the nSMOL Antibody BA Kit was used as a reaction solution.

The reaction solution was visually observed while step (b) was proceeding. As a result, it was observed that Immunoglobulin Collection Resin and FG beads Trypsin DART® precipitated at the bottom of the vessel, as the reaction solution was let stand longer.

Into the samples respectively reacted for 1 hour, 3 hours, and 5 hours, the Reaction Stop Solution (10% formic acid) was quickly added, and the solutions were collected to be subjected to LC-MS measurement using NexeraX2 system (Shimadzu Corporation) and LCMS-8050/8060 (Shimadzu Corporation). As a peptide fragment for quantifying trastuzumab (signature peptide), IYPTNGYTR (SEQ ID No. 1) existing in the CDR2 region of the heavy chain was selected.

Results of the LC-MS measurement are shown in FIG. 1. As understood from the results of FIG. 1, the highest ion yield was obtained under Condition A where the stirring was continuously carried out. However, the results of Conditions B and C were lower than that of Condition A only by 10 to 20%, and therefore it was confirmed that Conditions B and C are not problematic to be used for the measurement. Furthermore, because the higher values were obtained by increasing the reaction time under any of the conditions, it is understood that it can be dealt by adjusting the reaction time in step (b).

Example 2

An experiment similar to Example 1 was conducted using bevacizumab as a measurement target. Samples prepared by adding bevacizumab of 50 μg/ml concentration (manufactured by Chugai Pharmaceutical Co., Ltd.) in Human plasma (manufactured by Kohjin Bio Co., Ltd.) were used, and the Reaction Solution contained in the nSMOL Antibody BA Kit was used as a reaction solution. As a signature peptide for quantifying bevacizumab, FTFSLDTSK (SEQ ID No. 2) existing in the CDR2 region of the heavy chain was selected.

Figure 2:
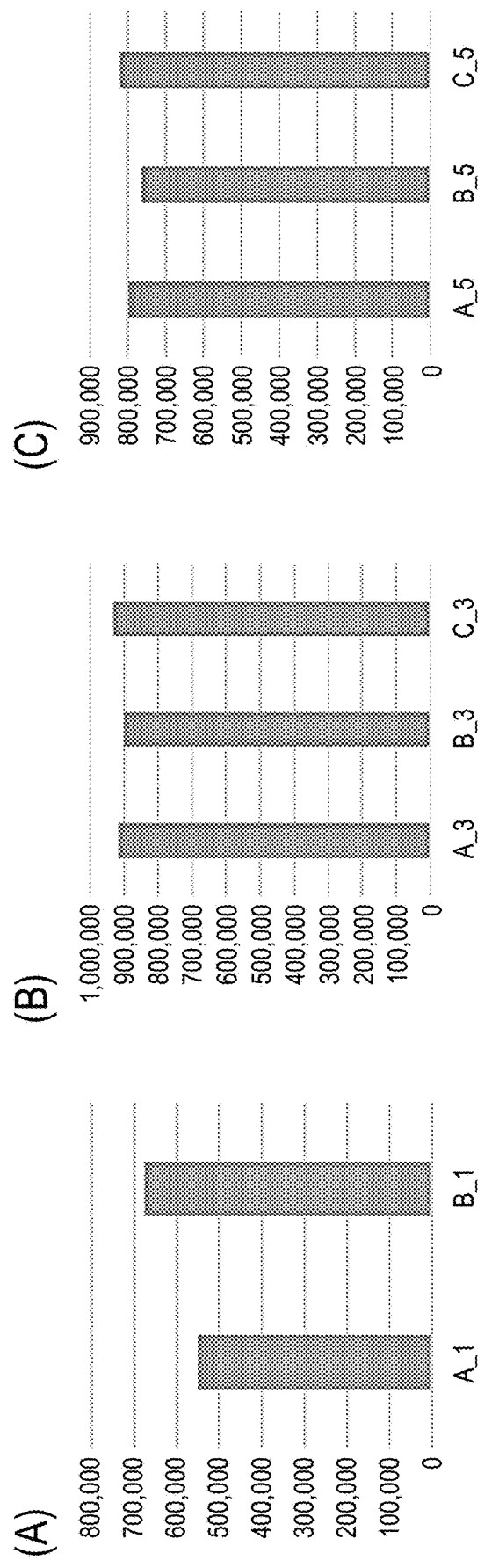
FIG. 2 shows results of bevacizumab analysis under 3 reaction conditions. (A): step (b) is carried out for 1 hour; (B): step (b) is carried out for 3 hour; and (C): step (b) is carried out for 5 hour. A_1, A_3, and A_5 indicate results of cases where stirring was carried out throughout the analysis. B_1, B_3, and B_5 indicate results of cases where 10-sec stirring was carried out every 1 hour. C_3 and C_5 indicate results of cases where the samples were let stand after initial stirring. The vertical axes indicate the relative peak intensity.

Results of the LC-MS measurement are shown in FIG. 2. In this Example, no significant differences due to the stirring conditions in the detection results were observed.

Example 3

An experiment similar to Example 1 was conducted under Conditions A and C, using adalimumab as a measurement target. Samples prepared by adding adalimumab of 50 µg/ml concentration (manufactured by AbbVie GK) in Human plasma (manufactured by Kohjin Bio Co., Ltd.) were used, and the Enhanced Reaction Solution contained in the nSMOL Antibody BA Kit was used as a reaction solution. As a signature peptide for quantifying adalimumab, APYTFGQGTK (SEQ ID No. 3) existing in the CDR3 region of the light chain was selected.

Figure 3:
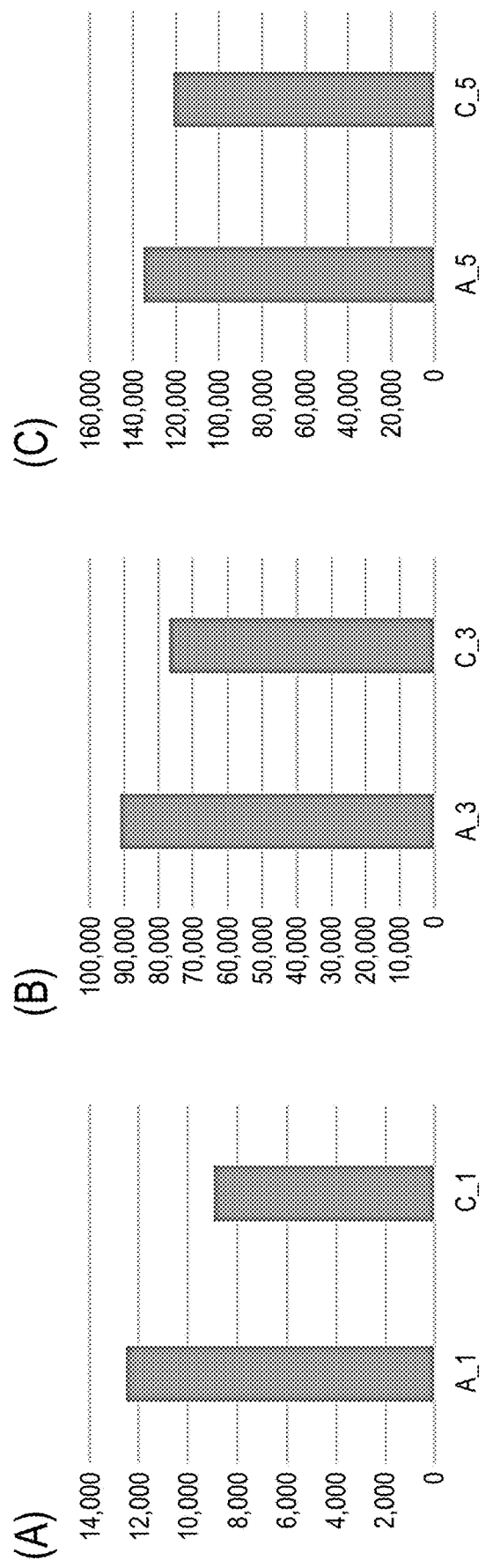
FIG. 3 shows results of adalimumab analysis under 2 reaction conditions. (A): step (b) is carried out for 1 hour; (B): step (b) is carried out for 3 hour; and (C): step (b) is carried out for 5 hour. A_1, A_3, and A_5 indicate results of cases where stirring was carried out throughout the analysis. C_1, C_3, and C_5 indicate results of cases where the samples were let stand after initial stirring. The vertical axes indicate the relative peak intensity.

Results of the LC-MS measurement are shown in FIG. 3. As understood from the results of FIG. 1, high ion yield was obtained under Condition A where the stirring was continuously carried out. However, the result of Condition C was lower than that of Condition A only by 10 to 20%, and therefore it was confirmed that Condition C is not problematic to be used for the measurement. Furthermore, because the higher values were obtained by increasing the reaction time under any of the conditions, it is understood that it can be dealt by adjusting the reaction time in step (b).

Example 4

An experiment similar to Example 1 was conducted under Conditions A and C, using nivolumab as a measurement target. Samples prepared by adding nivolumab of 50 µg/ml concentration (manufactured by ONO PHARMACEUTICAL CO., LTD.) in Human plasma (manufactured by Kohjin Bio Co., Ltd.) were used, and the Enhanced Reaction Solution contained in the nSMOL Antibody BA Kit was used as a reaction solution. As a signature peptide for quantifying nivolumab, ASGITFSNSGMHWVR (SEQ ID No. 4) existing in the CDR1 region of the heavy chain was selected.

Figure 4:
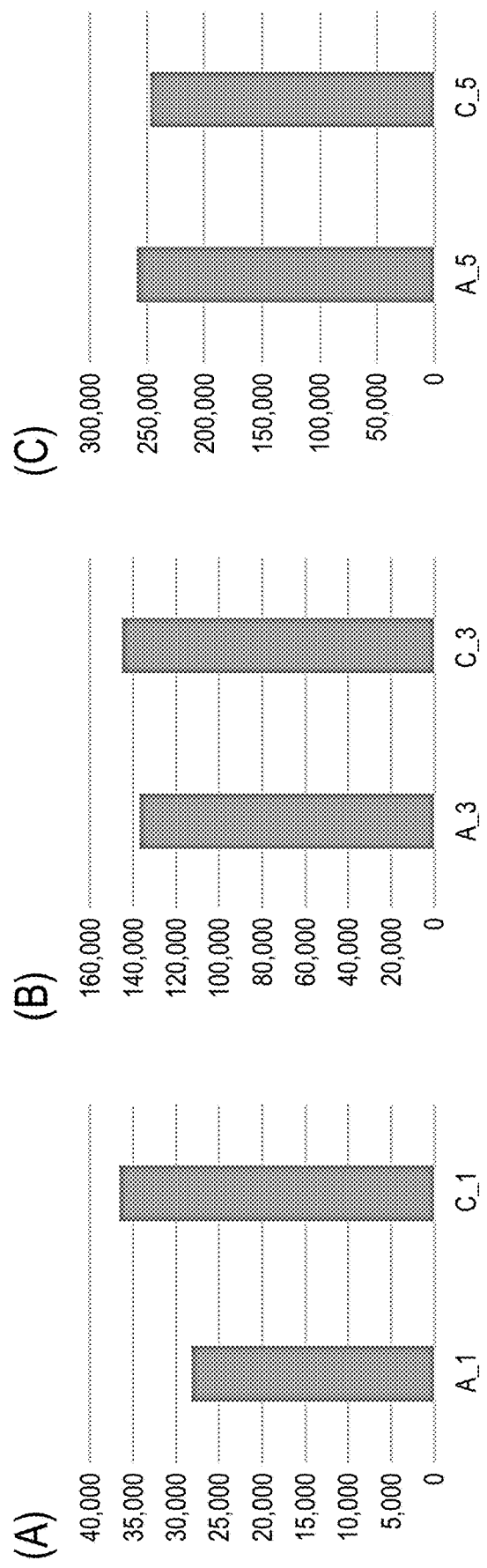
FIG. 4 shows results of nivolumab analysis under 2 reaction conditions. (A): step (b) is carried out for 1 hour; (B): step (b) is carried out for 3 hour; and (C): step (b) is carried out for 5 hour. A_1, A_3, and A_5 indicate results of cases where stirring was carried out throughout the analysis. C_1, C_3, and C_5 indicate results of cases where the samples were let stand after initial stirring. The vertical axes indicate the relative peak intensity.

Results of the LC-MS measurement are shown in FIG. 4. In this Example, no significant differences due to the stirring conditions in the detection results were observed.

Example 5

An experiment similar to Example 1 was conducted under Conditions A and C, using infliximab as a measurement target. Samples prepared by adding infliximab of 50 µg/ml concentration (manufactured by Mitsubishi Tanabe Pharma Corporation) in Human plasma (manufactured by Kohjin Bio Co., Ltd.) were used, and the Enhanced Reaction Solution contained in the nSMOL Antibody BA Kit was used as a reaction solution. As a signature peptide for quantifying infliximab, SINSATHYAESVK (SEQ ID No. 5) existing in the CDR2 region of the heavy chain was selected.

Figure 5:
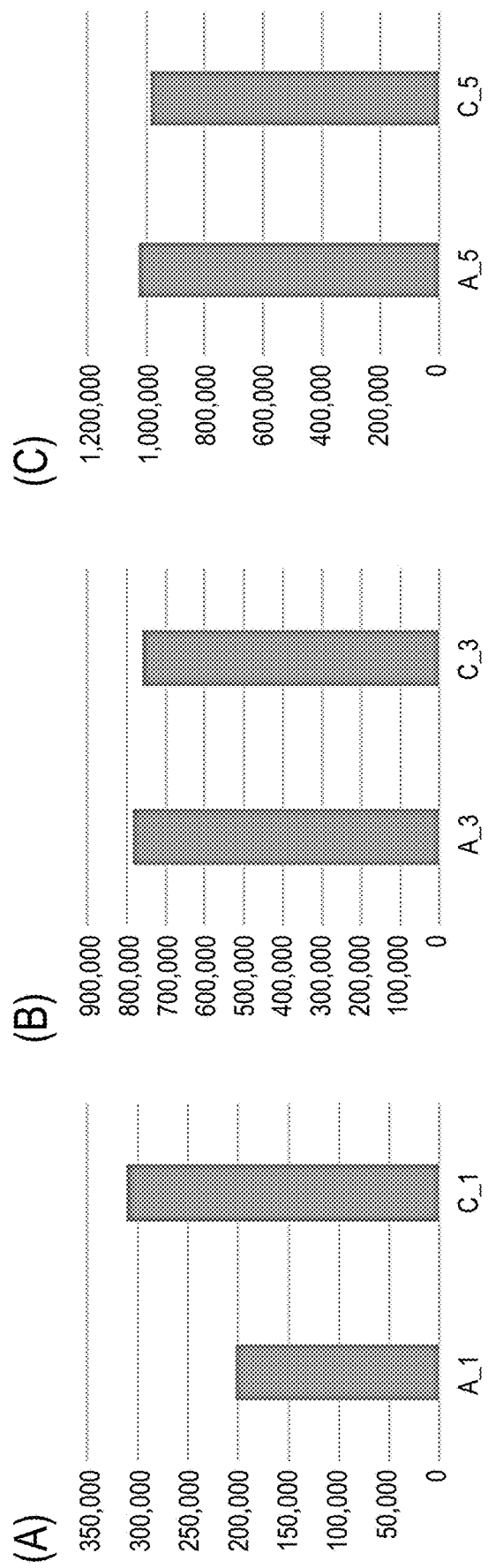
FIG. 5 shows results of infliximab analysis under 2 reaction conditions. (A): step (b) is carried out for 1 hour; (B): step (b) is carried out for 3 hour; and (C): step (b) is carried out for 5 hour. A_1, A_3, and A_5 indicate results of cases where stirring was carried out throughout the analysis. C_1, C_3, and C_5 indicate results of cases where the samples were let stand after initial stirring. The vertical axes indicate the relative peak intensity.

Results of the LC-MS measurement are shown in FIG. 5. In this Example, no significant differences due to the stirring conditions in the detection results were observed.

Example 6

An experiment similar to Example 1 was conducted under Conditions A and C, using rituximab as a measurement target. Samples prepared by adding rituximab of 50 µg/ml concentration (manufactured by Zenyaku Kogyo Co., Ltd.) in Human plasma (manufactured by Kohjin Bio Co., Ltd.) were used, and the Enhanced Reaction Solution contained in the nSMOL Antibody BA Kit was used as a reaction solution. As a signature peptide for quantifying rituximab, GLEWIGAIYPGNGDTSYNQK (SEQ ID No. 6) existing in the CDR2 region of the heavy chain was selected.

Figure 6:
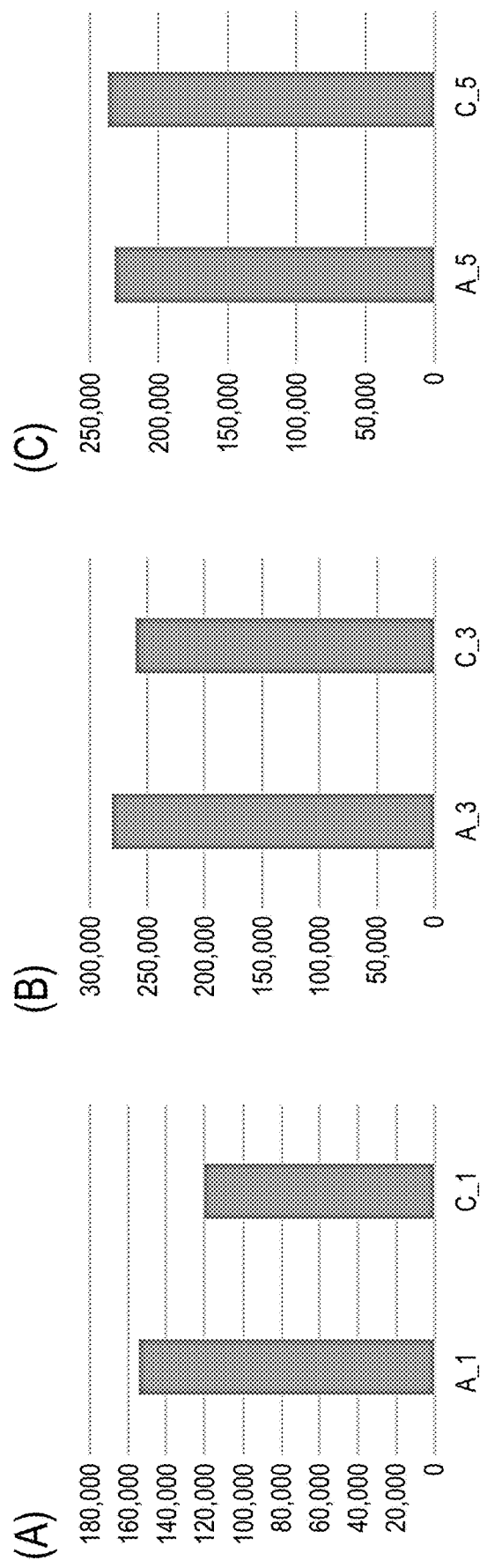
FIG. 6 shows results of rituximab analysis under 2 reaction conditions. (A): step (b) is carried out for 1 hour; (B): step (b) is carried out for 3 hour; and (C): step (b) is carried out for 5 hour. A_1, A_3, and A_5 indicate results of cases where stirring was carried out throughout the analysis. C_1, C_3, and C_5 indicate results of cases where the samples were let stand after initial stirring. The vertical axes indicate the relative peak intensity.

Results of the LC-MS measurement are shown in FIG. 6. As understood from the results of FIG. 6, high ion yield was obtained under Condition A where the stirring was continuously carried out. However, the result of Condition C was lower than that of Condition A only by 10 to 20%, and therefore it was confirmed that Condition C is not problematic to be used for the measurement. Furthermore, because the higher values were obtained by increasing the reaction time under any of the conditions, it is understood that it can be dealt by adjusting the reaction time in step (b).

INDUSTRIAL APPLICABILITY

The present invention improves the protocol of the nSMOL method, so that the detection method of a monoclonal antibody using mass spectrometry is simplified and expected to be applicable to multisample analysis and automated analysis, especially to automatic dispensers. Especially, the present invention gives the nSMOL method a wider applicability in pharmacokinetic studies and therapeutic drug monitoring studies.

All publications, patents and patent applications cited in the present specification are incorporated herein by reference in their entirety.

The invention claimed is:

1. A method for detecting a monoclonal antibody in a sample, the method comprising:
   (a) a step of capturing and immobilizing, in pores of a porous body, the monoclonal antibody in the sample;
   (b) a step of performing selective protease digestion of the monoclonal antibody for 30 min or longer by contacting the porous body having the monoclonal antibody immobilized thereon with nanoparticles having a protease immobilized thereon; and
   (c) a step of detecting a peptide fragment obtained by the selective protease digestion, using liquid chromatography mass spectrometry (LC-MS),
   wherein step (b) is carried out under stirring condition for 10 sec to 5 min in a initial reaction stage, and then under static condition.

2. The method according to claim 1, wherein step (b) further comprises additional stirring for 10 sec to 1 min one or more times in addition to the stirring for 10 sec to 1 min in the initial reaction stage.

3. The method according to claim 1, wherein the stirring is carried out by pipetting operation performed by an automatic dispenser.

4. The method according to claim 1, wherein step (b) is carried out in a heating vessel that is set to a predetermined reaction temperature.

5. The method according to claim 1, wherein the method is capable of quantifying the monoclonal antibody in the sample having an antibody concentration in the range of 0.05 to 300 µg/ml.

* * * * *

SEQUENCE LISTING

<160> NUMBER OF SEQ ID NOS: 6

<210> SEQ ID NO 1
<211> LENGTH: 9
<212> TYPE: PRT
<213> ORGANISM: Artificial
<220> FEATURE:
<223> OTHER INFORMATION: Trastuzumab signature peptide

<400> SEQUENCE: 1

Ile Tyr Pro Thr Asn Gly Tyr Thr Arg
1               5

```
<210> SEQ ID NO 2
<211> LENGTH: 9
<212> TYPE: PRT
<213> ORGANISM: Artificial
<220> FEATURE:
<223> OTHER INFORMATION: Bevacizumab signature peptide

<400> SEQUENCE: 2

Phe Thr Phe Ser Leu Asp Thr Ser Lys
1               5

<210> SEQ ID NO 3
<211> LENGTH: 10
<212> TYPE: PRT
<213> ORGANISM: Artificial
<220> FEATURE:
<223> OTHER INFORMATION: Adalimumab signature peptide

<400> SEQUENCE: 3

Ala Pro Tyr Thr Phe Gly Gln Gly Thr Lys
1               5                   10

<210> SEQ ID NO 4
<211> LENGTH: 15
<212> TYPE: PRT
<213> ORGANISM: Artificial
<220> FEATURE:
<223> OTHER INFORMATION: Nivolumab signature peptide

<400> SEQUENCE: 4

Ala Ser Gly Ile Thr Phe Ser Asn Ser Gly Met His Trp Val Arg
1               5                   10                  15

<210> SEQ ID NO 5
<211> LENGTH: 13
<212> TYPE: PRT
<213> ORGANISM: Artificial
<220> FEATURE:
<223> OTHER INFORMATION: Infliximab signature peptide

<400> SEQUENCE: 5

Ser Ile Asn Ser Ala Thr His Tyr Ala Glu Ser Val Lys
1               5                   10

<210> SEQ ID NO 6
<211> LENGTH: 20
<212> TYPE: PRT
<213> ORGANISM: Artificial
<220> FEATURE:
<223> OTHER INFORMATION: Rituximab signature peptide

<400> SEQUENCE: 6

Gly Leu Glu Trp Ile Gly Ala Ile Tyr Pro Gly Asn Gly Asp Thr Ser
1               5                   10                  15

Tyr Asn Gln Lys
            20
```